United States Patent
Hulten (10) Patent No.: US 7,083,924 B2
(45) Date of Patent: Aug. 1, 2006

(54) DIAGNOSTIC METHOD FOR THE IDENTIFICATION OF FOETAL DNA IN A MATERIAL SAMPLE

(75) Inventor: Maj Anita Hulten, Birmingham (GB)

(73) Assignee: BTG International Limited, London (GB)

( * ) Notice: Subject to any disclaimer, the term of this patent is extended or adjusted under 35 U.S.C. 154(b) by 0 days.

(21) Appl. No.: 10/332,533

(22) PCT Filed: Jul. 9, 2001

(86) PCT No.: PCT/GB01/03092

§ 371 (c)(1),
(2), (4) Date: Apr. 10, 2003

(87) PCT Pub. No.: WO02/04672

PCT Pub. Date: Jan. 17, 2002

(65) Prior Publication Data

US 2003/0152981 A1    Aug. 14, 2003

(30) Foreign Application Priority Data

Jul. 10, 2000  (GB) ................. 0016742.9

(51) Int. Cl.
  *C12Q 1/68* (2006.01)
  *C12P 19/34* (2006.01)
(52) U.S. Cl. .................. 435/6; 435/91.1; 435/91.2
(58) Field of Classification Search ............ 435/6, 435/91.1, 91, 2, 91.2
  See application file for complete search history.

(56) References Cited

U.S. PATENT DOCUMENTS

2003/0186287 A1* 10/2003 Lin et al. ............... 435/6
2004/0018509 A1*  1/2004 Bianchi ................. 435/6

FOREIGN PATENT DOCUMENTS

| EP | 0430402 A | 6/1991 |
| WO | 94/02646 A | 2/1994 |
| WO | 98/39474 A | 9/1998 |

OTHER PUBLICATIONS

Verma et al., "Rapid and simple prenatal DNA diagnosis of Down's syndrome", The Lancet, vol. 352, (1998), pp. 9-12.
Poon et al., "Prenatal detection of fetal Down's syndrome from maternal plasma", The Lancet, vol. 356, (2000), pp. 1819-1821.
Youngren, Kjell et al.; "Synchrony In Telomers Length of the Human Fetus"; *Human Genetics*; vol. 102, No. 6; Jun. 1998; pp. 640-643; (XP002200862).
Iwama, Hiroshi et al.; "Telomeric Length and Telomerase Activity Vary With Age in Peripheral Blood Cells Obtained from Normal Individuals"; *Human Genetics*; vol. 102, No. 4; Apr. 1998; pp. 397-402; (XP002200863).

* cited by examiner

*Primary Examiner*—Jezia Riley
(74) *Attorney, Agent, or Firm*—Nixon & Vanderhye P.C.

(57) ABSTRACT

A method for the identification of foetal DNA in a maternal DNA-containing sample such as a blood or vaginal sample, said method comprising (a) isolating DNA from said sample, (b) subjecting said DNA to exonucleolytic digestion by an enzyme so as to remove end regions of each DNA molecule, and (c) detecting the presence of a DNA sequence remaining in foetal DNA but absent form maternal DNA as a result of said digestion process. Once identified, the foetal DNA can be subject to diagnosis for example to detect chromosomal/DNA abnormalities, including in particular aneuploides such as foetal trisomy 21.

40 Claims, 5 Drawing Sheets

Figure 1(A)

M 1    M 2+F    F-Pat
Length of chromosome 21 specific polymorphic DNA marker in base pairs

Figure 1(B)

M 1+F    M 2+F    F-Pat
Length of chromosome 21 specific polymorphic DNA marker in base pairs

Figure 1(C)

M 1    M 2+F    F-Pat
Length of chromosome 21 specific polymorphic DNA marker in base pairs

Figure 1(D)

Length of chromosome 21 specific polymorphic DNA marker is base pairs

DIAGNOSTIC METHOD FOR THE IDENTIFICATION OF FOETAL DNA IN A MATERIAL SAMPLE

The present specification is a 371 U.S. national phase of PCT/GB01/03092, filed Jul. 9, 2001.

The present invention relates to a method for the identification of foetal DNA, in a maternal sample such as a blood or vaginal sample. Foetal DNA identified in this way can then be used, for instance, in pre-natal diagnosis.

Chromosome disorders are among the most common genetic disease in humans. Constitutional chromosome disorders range in incidence from more than 50% of the lethality associated with miscarriage during the first trimester of pregnancy as well as around 5% of intrauterine or perinatal deaths. In addition at least 0.5% of liveborn children have a constitutional chromosome abnormality associated with mental and/or physical disability.

Chromosome abnormalities may be either numerical or structural. Numerical abnormalities, implying a change from the normal diploid chromosome number of 46 in somatic tissues include trisomies (one extra chromosome), monosomies (one chromosome missing) and polyploidy (whole extra set of chromosomes). Structural rearrangements, caused by chromosome breakage followed by healing of the broken chromosome ends in aberrant positions, include so called translocations, inversions and insertions. Structural chromosome rearrangements can occur in balanced form, in which case the genetic material usually remains the same as normal.

Carriers of balanced structural chromosome rearrangement are physically and mentally normal but may suffer reproductive problems with an increased risk for reduced fertility as well as an increased risk for chromosomally unbalanced offspring, leading to miscarriage, intra-or perinatal death and/or liveborn children with physical and/or mental disability.

The most common chromosome abnormality occurring as an entity in the human population is trisomy 21, associated with Down Syndrome. It is generally accepted that around 1/650 liveborn children has trisomy 21 Down Syndrome characterised by more or less severe psychomotor development delay. There is no substantial difference in the incidence of trisomy 21 Down Syndrome in different countries world-wide.

The diagnosis of trisomy 21 Down Syndrome in child- and adulthood is usually performed by chromosome analysis following in vitro culture of blood lymphocytes. The cell culture procedure takes 2–3 days to allow accumulation of enough cells in the metaphase stage of the cell cycle, when chromosomes are sufficiently condensed for their individual identification by standard chromosome banding technology.

The only clearly documented clinical risk factor for having a child with regular trisomy 21 Down Syndrome concerns maternal age. Thus it is generally accepted that there is an increasing risk for having a trisomy 21 child with advancing maternal age, which in the highest age group of more than 45 years may be over 10% of pregnancies. This situation has led to intensive screening programmes of pregnant women to identify those that are most likely to be carrying a child with trisomy 21. These screening programmes include analysis of maternal blood samples for biochemical characteristics as well as ultrasonography of the foetus with the aim especially to look at the accumulation of fluid under the skin of the neck, which is characteristically increased in foetuses with Down Syndrome and some other common aneuploidies.

In addition pregnant women over a certain age, usually 35 years, are routinely offered invasive procedures (chorionic villus sampling and/or amniocentesis) to allow foetal cell sampling for chromosome analysis. The most common current method for performing prenatal diagnosis of chromosome disorders concerns karyotyping, following in vitro culture of amniotic fluid samples. This involves microscopy analysis of mitotic cells, where chromosomes are sufficiently condensed. Cell cultures occupy around 1–3 weeks, and the long delay in diagnosis is recognised as being associated with much parental anxiety.

Alternative technologies for more rapid prenatal chromosome diagnosis include (1) fluorescence in situ hybridisation (FISH) of resting (interphase) cell nuclei from uncultured amniotic fluid samples, and (2) DNA diagnosis using DNA isolated from amniotic fluid samples, amplified by for example the polymerase chain reaction (PCR) and quantity of chromosome-specific primers determined by Q-PCR techniques.

These two alternatives for prenatal diagnosis for chromosome disorders, using amniotic fluid samples, may imply that reports can be issued rapidly, within the same or the following day after the sample has arrived in the laboratory. So far they have been limited to the rapid diagnosis of the most common chromosome abnormalities, i.e. those involving trisomies 21, 13, 18 and sex chromosome aneuploidy.

In any case, invasive methods such as amniocentesis and chorionic villus sampling, as well as being uncomfortable for the mother, are associated with an increased risk of miscarriage of around 1–1.5%. There is a need therefore to provide a more efficient way of carrying out pre-natal diagnosis without resorting to such invasive sampling methods.

Samples obtained using less invasive methods from the pregnant mother will commonly contain a vast majority of maternal cells with a relatively small number of foetal cells, in the order of 1 per 10,000 to 1 per 10 million. Current methods for foetal cell isolation include the use of antibodies, gradient fractionation, preferential maternal cell lysis, magnetic activated cell sorting (MACS), ferrofluid suspension with magnet, micromanipulation of individual cells, charged flow separation and fluorescence activated cell sorting (FACS). However, maternal cells still tend to dominate any foetal cells recovered. In addition, many of these techniques are time consuming and labour intensive.

It has more recently been recognised that maternal blood samples, in particular plasma or serum contain relatively large amounts of foetal DNA (Lo et al., Lancet 1997, 350, 485–487, WO 98/39474). It has further been demonstrated that this foetal DNA, following in vitro amplification by techniques such as PCR may be identified with respect to foetus-specific sequences. This technology has been applied on several occasions for diagnosis of foetal sex by Y-chromosome specific primers, and other conditions such as Haemoglobinopathies, where prenatal diagnosis is based on specific mutations in foetal DNA.

In addition it has been shown that foetal chromosome abnormalities such as trisomy 21 is associated with an increase in foetal DNA in maternal serum/plasma in comparison to the normal situation using foetal-specific primers as exemplified above. Furthermore complications in pregnancy such as pre-eclampsia and preterm labour and the post partum development of autoimmune disease, may also be characterised by increased fetomaternal transfusion, leading to higher levels of fetal cells in maternal blood (reviews in Pertl and Bianchi Semin Perinatol 23, 5, 393–402, 1999; Bianchi Eur J Obstet Gynecol Reprod Biol 92, 1, 103–8, 2000).

Figure 1A:
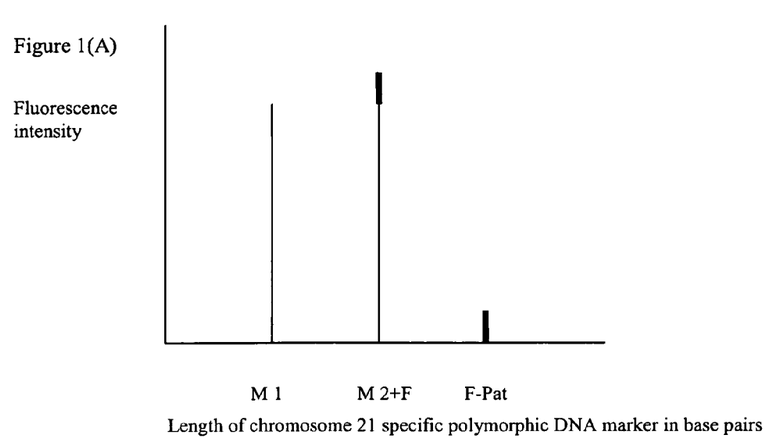
FIGS. 1(A)–1(D) show a comparative example of Genescan analysis of DNA extracted from maternal blood FIG. 1(A) where the foetus is normal, FIG. 1(B) where the foetus has trisomy 21, as carried out using prior art method, FIG. 1(C) where the foetus has trisomy 21, as carried out using prior art method, and FIG. 1(D) where the foetus has trisomy 21, as carried out using prior art method.

It has been concluded that the amount of foetal DNA, ascertained by foetal-specific DNA primers, (such as Y-chromosome specific primers in male foetuses) may be used as a screening method for the detection of pregnancies, where there is an increased risk for foetal chromosome aneuploidy. Most importantly however, it has not been possible to diagnose foetal aneuploidy per se by said methods. Thus these methods are not sensitive enough to measure the difference between foetal DNA, to determine whether the foetus is normal or aneuploid. Examples of the sorts of results these tests give are illustrated in FIG. 1 hereinafter. In FIG. 1(A), the foetus is normal and there are two peaks corresponding to the maternal alleles. One of these (M2) is larger than the other (M1) and there is an additional amount of DNA originating from the foetal DNA (F). The size of this is the same as the peak originating from the foetal allele of paternal origin (F-Pat).

Figure 1B:
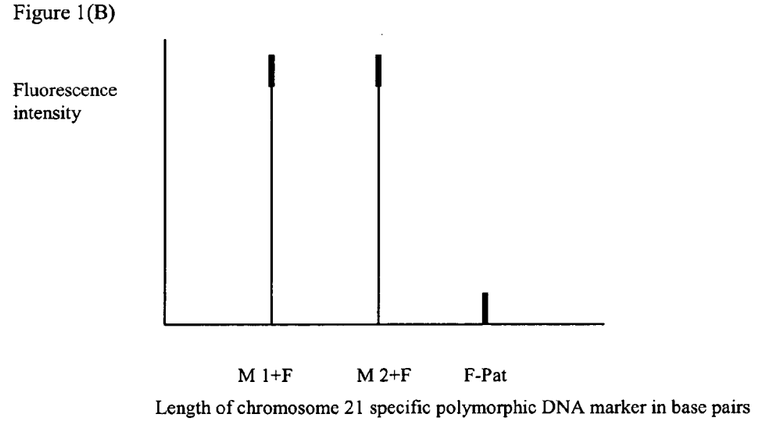
Figure 1C:
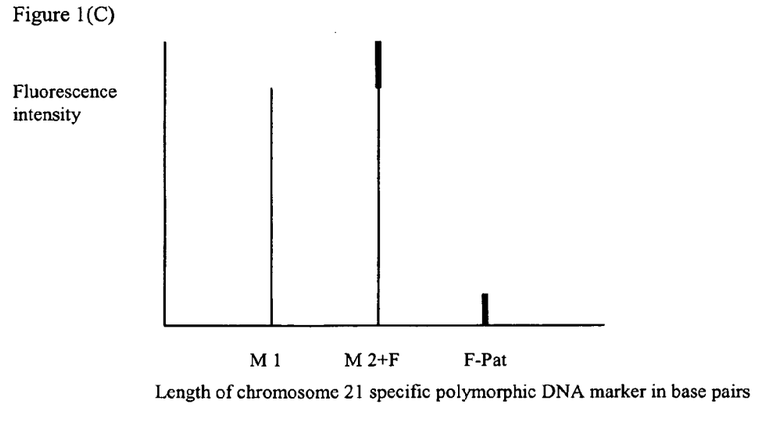
Figure 1D:
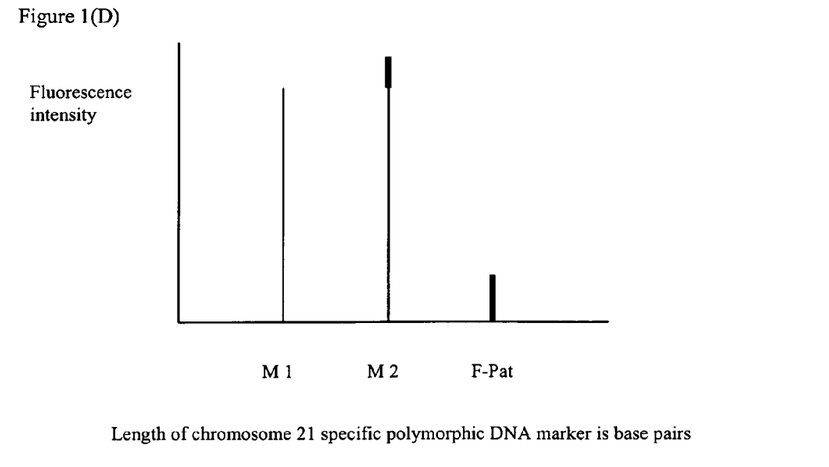

In FIG. 1(B), the foetus has trisomy 21 with one copy of F on each of the maternal alleles M1 and M2, plus one copy of paternal origin (F-Pat). This will reduce the difference in fluorescence between the alleles M1 and M2 in comparison to the normal situation illustrated in (a). In FIG. 1(C), the foetus has trisomy 21 with two copies of F on maternal allele M2, plus one copy of paternal origin (F-Pat). This increases the difference in fluorescence between the alleles M1 and M2 in comparison to the normal situation illustrated in FIG. 1(A). Finally in FIG. 1(D), the foetus has trisomy 21 with 2 copies of paternal origin F-Pat. This makes no difference to the fluorescence from the maternal alleles M1 and M2, but the fluorescence of the paternal allele is doubled. Such results are very difficult to interpret, and there is to our knowledge no documented case where prenatal diagnosis of trisomy 21 (or any other aneuploidy) has been diagnosed in this way, using a maternal blood or vaginal sample.

There is therefore an urgent need for new methods to identify foetal DNA in a maternal DNA-containing sample such as a blood or vaginal sample, comprising a novel way of non-invasive prenatal diagnosis.

It is well known that the telomeres, constituting repeated DNA sequences that cap the ends of chromosomes, vary such that young people have a higher number of the repeats than older people. It is thought that DNA replication is not taking place at the very ends of the telomere repeats. This means that, at each cell division, the telomeres become shorter than before. It is also thought that this shortening eventually leads to cell death.

Telomeres of all human chromosomes contain the same DNA core repeat TTAGGG. The variation in telomere length with age of the individual is a general phenomenon observed on all the chromosomes. Depending upon the age of the individual, variation in repeat length of telomeres is estimated to be in the order of 4–200 Kb of DNA.

Chromosome-specific telomere lengths can be measured using special software and microscopy image analysis of chromosomes hybridised with telomeric probes or commercially available peptide nucleic acid probes (PNA, DAKO Ltd). These investigations indicate that there may be some variation between individual cell nuclei in the telomere content of individual chromosomes. Nevertheless, as already mentioned, there is a substantial decrease in telomere length with the age of the subject.

On this basis, the telomere length of individual chromosomes in foetal cells should be longer than in the newborn child, and longer still than in the adult. It is implicit therefore that foetal cells have longer telomeres, i.e. a higher copy number per chromosomes of the telomere DNA repeats, than cells from the mother (Butler et al., Cancer Genetics and Cytogenetics 105, 138–144, 1998; Kreji and Koch, Chromosoma 107, 198–203, 1998).

The applicants have found that this characteristic can be used as a basis for differentiation between maternal and foetal DNA, in particular DNA, present in a maternal DNA-containing sample such as a blood (including plasma or serum) or vaginal sample.

Thus according to the present invention there is provided a method for the identification of foetal DNA in a maternal DNA-containing sample, said method comprising (a) isolating DNA from said sample, (b) subjecting said DNA to exonucleolytic digestion by an enzyme so as to remove end regions of said DNA, and (c) detecting the presence of a DNA sequence remaining in foetal DNA but absent from maternal DNA as a result of said digestion process.

Steps (a) and (b) may be conducted in any order. For example, DNA is first isolated from the cells and then subject to enzymatic digestion in accordance with step (b). However, alternatively, the digestion may be effected directly in cells, and digested DNA isolated for example by PCR amplification therefrom for analysis in step (c).

Suitably the maternal DNA-containing sample is a blood or vaginal sample. Preferably, the method is carried out using a maternal blood sample. The expression "blood sample" as used herein encompasses whole blood, or serum or plasma derived therefrom.

In a particularly preferred embodiment, cells are first separated from maternal plasma and DNA extracted from these as step (a), or if appropriate during or after step (b), of the process. Examples of such DNA amplification, which is advantageous when only a small amount of material is available, are described for instance in Findlay et al Mol Pathol 51 (3), 164–167, 1998, Klein et al Proc Natl Acad Sci USA 96 (8), 4494–4499, 1999.

However there may be cases were the invention is conveniently employed in the analysis of other prenatal sample types such as amniotic fluid. Generally amniotic fluid samples contain relatively little maternal DNA and identification of foetal DNA is not difficult. On some occasions however, the samples are contaminated with maternal blood, and give complicated fluorescence patterns when analysed for example using the Q-PCR method. Isolation of foetal DNA from such samples using a method of the invention as a preliminary step might be useful.

DNA may be isolated from the sample using conventional methods. Preferably techniques are employed which result in the isolation of long DNA fragments. An example of such a method is the use of agarose plugs as described by Heiskanen et al., Biotechniques 17, 5, 928–929; 9320933, 1994.

Figure 2:
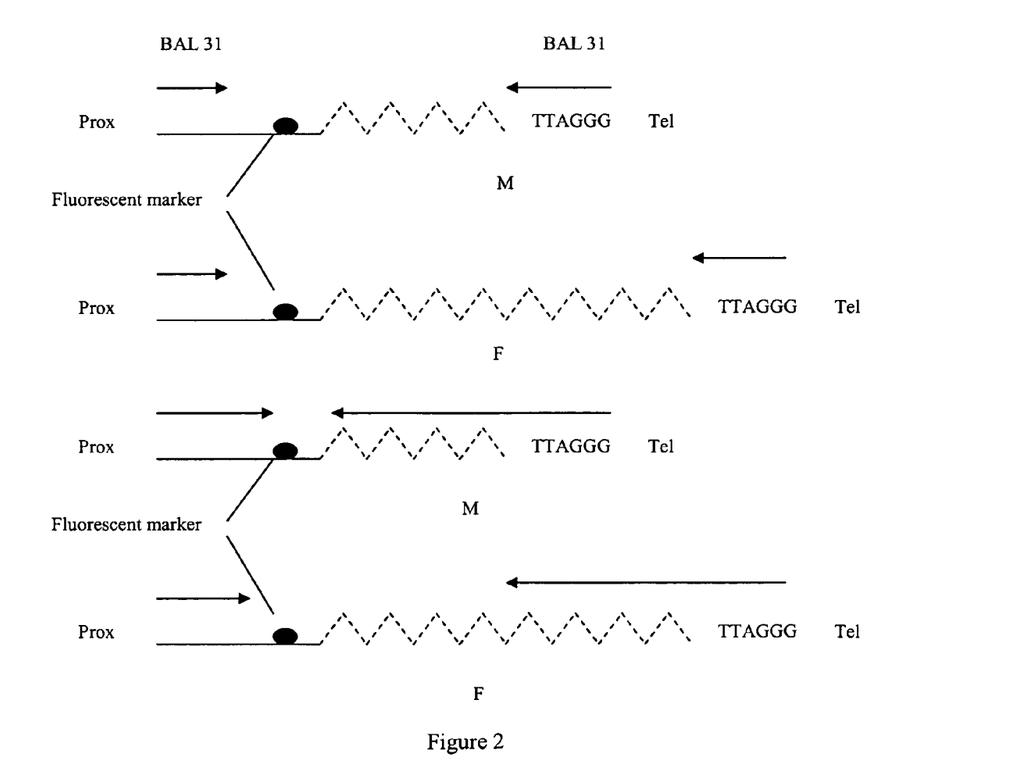
FIG. 2 illustrates diagrammatically the exonucleolytic digestion of DNA fragments such as Bal31, where fragments are digested at both ends: although there are fewer telomeric sequences in the maternal sequences (M) in comparison to the foetal sequence (F) and so allow foetal DNA to be identified, differentiation between M and F fluorescent marker signals, if positioned as shown, would not be possible.

In one embodiment, the DNA from step (a) is cut using a restriction enzyme into fragments prior to step (b). Thus the exonucleolytic digestion removes terminal regions of the DNA fragments (See FIG. 2 hereinafter). [However, this may not always be necessary, in particular where cells isolated from plasma are themselves directly subject to exonucleic digestion, and the resultant DNA amplified by PCR prior to analysis.]

In a particularly preferred embodiment, cut ends of the DNA fragments are protected prior to the exonucleolytic digestion so that they are not susceptible to digestion by exonucleolytic enzymes such as Bal31. This will mean that the digestion of fragments derived from the terminal regions of the DNA will be unidirectional, from the telomere region inwards. The proximal end will be protected from digestion, as will fragments derived from internal regions of the DNA. As a result, digestion will take place only in the telomere region (See FIG. 3 hereinafter).

Suitably, the restriction enzyme used to form the DNA fragments is one which cuts so as to provide binding sites for a protecting moiety, such as an adaptor. Protection can then be effected by ligation of a suitable adaptor. A suitable adaptor may be 2'-O-methyl ribonucleotide DNA (Mukai et al. Nucleic Acid Research Symposium Series 19, 1998) or complementary oligonucleotide containing phosphorothiate links.

Suitable DNA sequences remaining in foetal DNA which may be detected in step (c) is a telomere sequence or a chromosome marker located proximal to the telomere region, and is most preferably a subtelomeric sequence, in particular one which is unique to the specific chromosome.

Detection in step (c) may be effected by any of the known techniques. In a preferred embodiment however, foetal DNA is isolated and purified using magnetic separation techniques. A particular method by which this can be achieved involves the use of biotinylated primers as probes specific for telomeres. Hybridisation of primers will mean that the foetal DNA will have a biotin label which can be separated magnetically using streptavidin coated paramagnetic particles (PMPs) or beads (see for example FIG. 4).

In context of the methods of the invention, it is frequently the case that primers can be used to function as probes. It will be clear to the skilled person where this applies. Thus the term "primer" as used herein should be understood as referring to sequences which may have probe function, as well as sequences which are used as conventional primers for amplification reactions.

Once isolated in this way, the DNA fragments may be analysed. If necessary, they may first be subjected to amplification. Pure amplified foetal DNA obtained in this way may have a wide application in non-invasive prenatal genetic analysis and diagnosis. It may be particularly preferred to carry out quantitative analysis for example, using a fluorescence Q-PCR method for instance by Applied Biosystems DNA sequencers and the Genescan software, as well a Pyrosequencing and other such methods including Microarrays. Many of these methods are now becoming fully automated.

In effect, the invention uses differences in the number of telomere repeats in foetal and maternal DNA as a basis for identification of foetal DNA in maternal DNA-containing samples. During step (b), DNA, preferably in the form of fragments and most preferably long fragments, is digested, preferably unidirectionally following protection of cut ends, from the telomeric end regions of the fragments inwards.

Telomere regions of all chromosomes present in the sample are digested first during this process. Exonucleolytic digestion may be carried out for a period of time sufficient to eliminate at least all maternal telomeric DNA sequences.

Figure 3A:
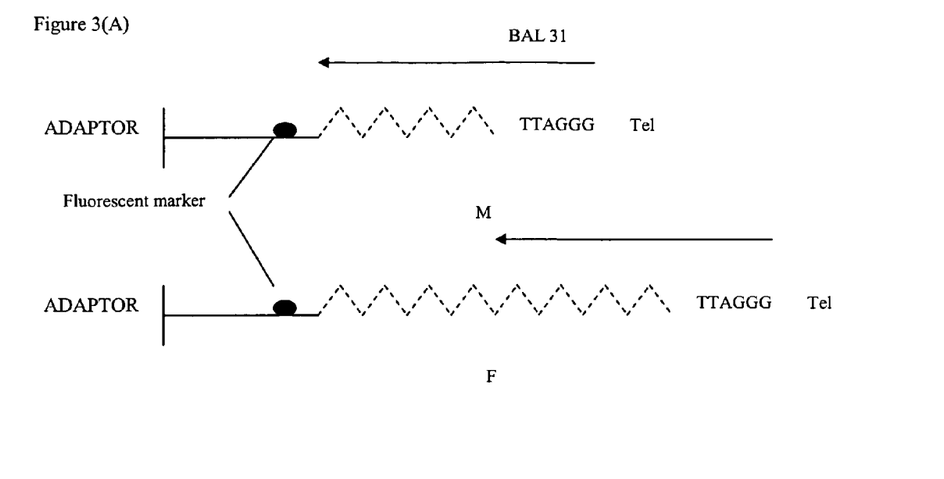
FIGS. 3(A) and 3(B) illustrate diagrammatically the unidirectional exonucleolytic digestion of DNA fragments using an adaptor in accordance with a preferred embodiment of the invention; such that in an optimal time course, FIG. 3(A), the enzyme will eliminate all M telomeric sequences and also FIG. 3(B) the M fluorescent marker signal. Such a system will allow differentiation of M and F fragments with selective retention of F fluorescent signal allowing enumeration of the F chromosomes concerned following DNA amplification e.g. by Q-PCR.

If digestion is halted at this point, some foetal DNA fragments will retain some telomeric DNA (FIG. 3(A)). This DNA is then detectable using for example, a labelled primer specific for the primer telomere DNA which will therefore hybridise only to foetal DNA.

Figure 3B:
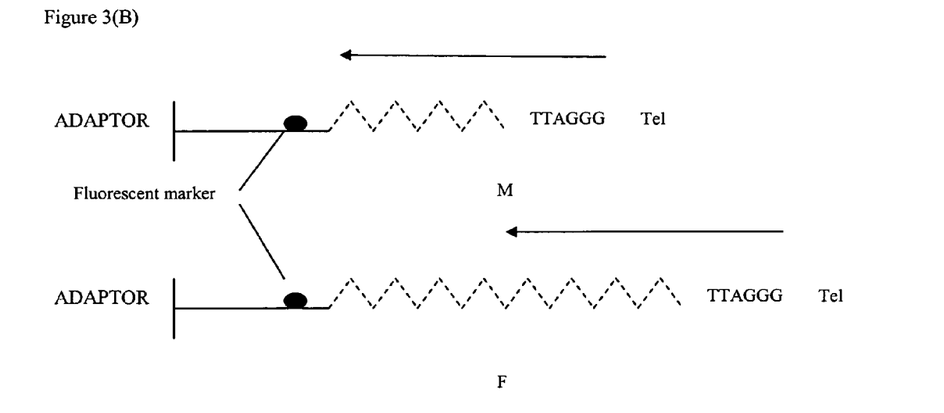

Digestion may however be continued such that subtelomeric DNA sequences are eliminated from all fragments of maternal DNA (FIG. 3(B)). In this instance, because digestion of the longer foetal telomeres takes longer, some chromosome-specific DNA will remain at the corresponding site in fragments of foetal DNA and so will be detectable for example using a primer for that DNA which therefore acts as a marker. The primer would not hybridise to maternal DNA under these circumstances. Preferably, primers used in the detection are labelled with visible labels such as fluorescent labels.

Where the sequence detected in step (c) is a chromosome marker, it may be preferable that it is a sub-telomeric polymorphic chromosome marker, as this gives rise to the possibility that the marker can itself be readily useful in pre-natal diagnosis.

In any event, the identification of foetal DNA can be used as a preliminary step to pre-natal diagnosis of the identified DNA.

In a particularly alternative embodiment, DNA present in the sample after digestion is amplified with a first labelled DNA primer specific for the said DNA sequence, such as the telomeric and/or subtelomeric sequence. Most preferably the first primer is labelled with a visible label in particular a fluorescent label, and fluorescence from the amplified sample is detected.

Suitable enzymes for conducting exonucleotylic digestion include Bal31. It may be preferable to use enzymes which digest specific regions of the DNA only, in order to ensure a more controllable digestion process. In particular, digestion is effected in a three step process, in which, in a first step, 3' extension DNA is removed, in a second step, 3'–51 ss regions are excised and in a third step, ss regions are digested. Suitable enzymes for effecting the first and third steps include Mungbean nuclease, and for the second step, suitable enzymes include Exonuclease III.

The conditions, such as enzyme concentrations, buffer systems, temperature and time of incubation, required in order to provide reliable digestion to allow differentiation between maternal and foetal DNA, require careful selection and depend upon factors such as the particular enzyme being used.

As a result of the variation in the numbers of telomeric DNA sequence repeats between different DNA ends, it is desirable first to "calibrate" the enzyme system, preferably in a chromosome specific manner. Calibration of this type may be effected by analysing the results of exonucleolytic telomeric digestion of the isolated DNA under various conditions.

Another means of calibrating particular enzyme systems is to obtain base-line information on the telomeric length of each individual chromosome end in maternal and foetal tissue samples. This may be done using fluorescence in situ hybridisation (FISH) of telomeric DNA sequences at the metaphase stage of the cell cycle. At this stage the individual telomeres at each chromosome end may be highlighted using FISH with telomere-specific probes in combination with subtelomeric DNA probes. Measurements of telomeric sequences may be performed by Microscopy Image Analysis, using for example a Comparative Genomic Hybridisation (CGH) software programme.

Blood samples from foetuses subject to cordocentesis and cord blood samples, obtained at delivery, can also be utilised, with a view to obtaining additional base-line information on the normal variation in length of telomeric DNA sequences for each chromosome arm in maternal and foetal tissue samples.

The conditions of enzyme concentrations and exposure times required to eliminate a subtelomeric marker from maternal DNA can be determined in a similar manner. In this instance, amplification for example using the polymerase chain reaction (PCR) of the subtelomeric markers of the DNA product may be effected in order to distinguish between constitutional maternal DNA alleles and foetal DNA alleles. This experimentation will provide base-line information on the rate of removal of subtelomeric DNA sequences by the respective enzymatic digestion conditions applied.

Preferred subtelomeric markers include, for instance a small tandem repeat (STR) or a microsatellite. For this purpose, they may or may not be polymorphic markers as they are only used for evaluation of their rate of disappearance by the exonucleolytic digestion and for differentiation between constitutional maternal and foetal DNA.

Polymorphic diagnostic markers may be preferred however if the analysis is subsequently used for prenatal diagnosis. Examples of chromosome 21—specific polymorphic tetranucleotide repeat markers are D21S11, D21S1412, D21S1411 and D21S1414. IFNAR, which is a dinucleotide repeat also shows a simple amplification pattern, in contrast to most other smaller repeat markers, which may be associated with stutter bands. Other examples of polymophic markers include single nucleotide polymorphisms (SNPs), which occur with very high frequency in the human genome, and where an increasing number are currently being identified.

In this case, the concentration of the foetal marker may subsequently be determined, for example using quantitative PCR methods such as TAQMAN™. This information, can be useful in pre-natal diagnosis of foetal conditions where only the amount of certain DNA sequences are different between the foetus and the mother. A reliable quantification of amount of chromosome-unique foetal DNA is required for the non-invasive prenatal diagnosis of common foetal conditions, including aneuploidies, such as Trisomy 21 Down syndrome, using a maternal blood sample.

In a preferred option the subtelomeric markers in question should be located as distal as possible among the chromosome-unique DNA sequences within each chromosome arm. These markers will be preselected for each chromosome end separately with respect to locations and degree of polymorphisms in the population studied.

Suitably the DNA markers selected are strategically localised in subtelomeric chromosome positions, containing chromosome-specific unique DNA. These locations are preferred for two main reasons.

Firstly, markers, localised near to the telomeres but yet containing unique chromosome specific DNA, will facilitate the digestion procedure, as only limited exonucleolytic digestion will be required in comparison to that needed to selectively eliminate maternal, more proximal, interstitial, DNA. This will be particularly useful when unidirectional digestion is undertaken as described above.

Secondly, the use of polymorphic subtelomeric Chromosome/DNA markers will allow quantification of not only numerical chromosome aberrations (such as trisomies) but also unbalanced structural chromosome rearrangements such as unbalanced translocations. An unbalanced translocation may be identified as a duplication of dosage for one subtelomeric marker in combination with a deletion of dosage for another subtelomeric marker, dependent on which chromosomes are involved in the translocation. In addition, other relatively common chromosome aberrations should be identifiable this way. These include extra marker chromosomes such as foetal iso 12p, or iso 18p, both associated with severe foetal malformations, which would give rise to extra double dosages in relation to the normal situation.

Special exonucleolytic procedures may be required for the diagnosis of extra chromosome markers such as 15 inv dup, as this involves two extra doses of 15p telomeric DNA sequences. Such duplications of telomeric sequences alone are harmless with respect to foetal development, while markers that also contain chromosome 15-specific DNA, located in the proximal part of the q arm, are associated with foetal psychomotor development delay, which may be severe.

By appropriate selection of subtelomeric markers used in the prenatal foetal diagnosis, the majority of chromosome abnormalities, leading to foetal development disturbance may be determined using this method. The only chromosome abnormalities that may not be detectable using the method, applying subtelomeric DNA markers alone, are more proximal (interstitial) deletions and duplications that are unexpected and therefore their exact locations cannot be determined. Special modifications of the method will also be required to diagnose specified deletions and duplications, expected because either parent is a carrier.

Once identified using the method of the invention, foetal DNA, may be subject to pre-natal diagnosis, for example to determine the presence of chromosome aberrations such as aneuploidy, Down syndrome, Edward Syndrome or Klinefelter Syndrome or other information such as the sex of the foetus.

Suitably, DNA is separated prior to analysis, for example using a magnetic separation method. In particular, the DNA is amplified using a labelled primer such as a specific biotinylated primer. If say a telomeric primer is used at this point, only telomere-containing, i.e. foetal DNA fragments will be measured and labelled, assuming all the corresponding maternal DNA has been eliminated during the digestion.

Figure 4:
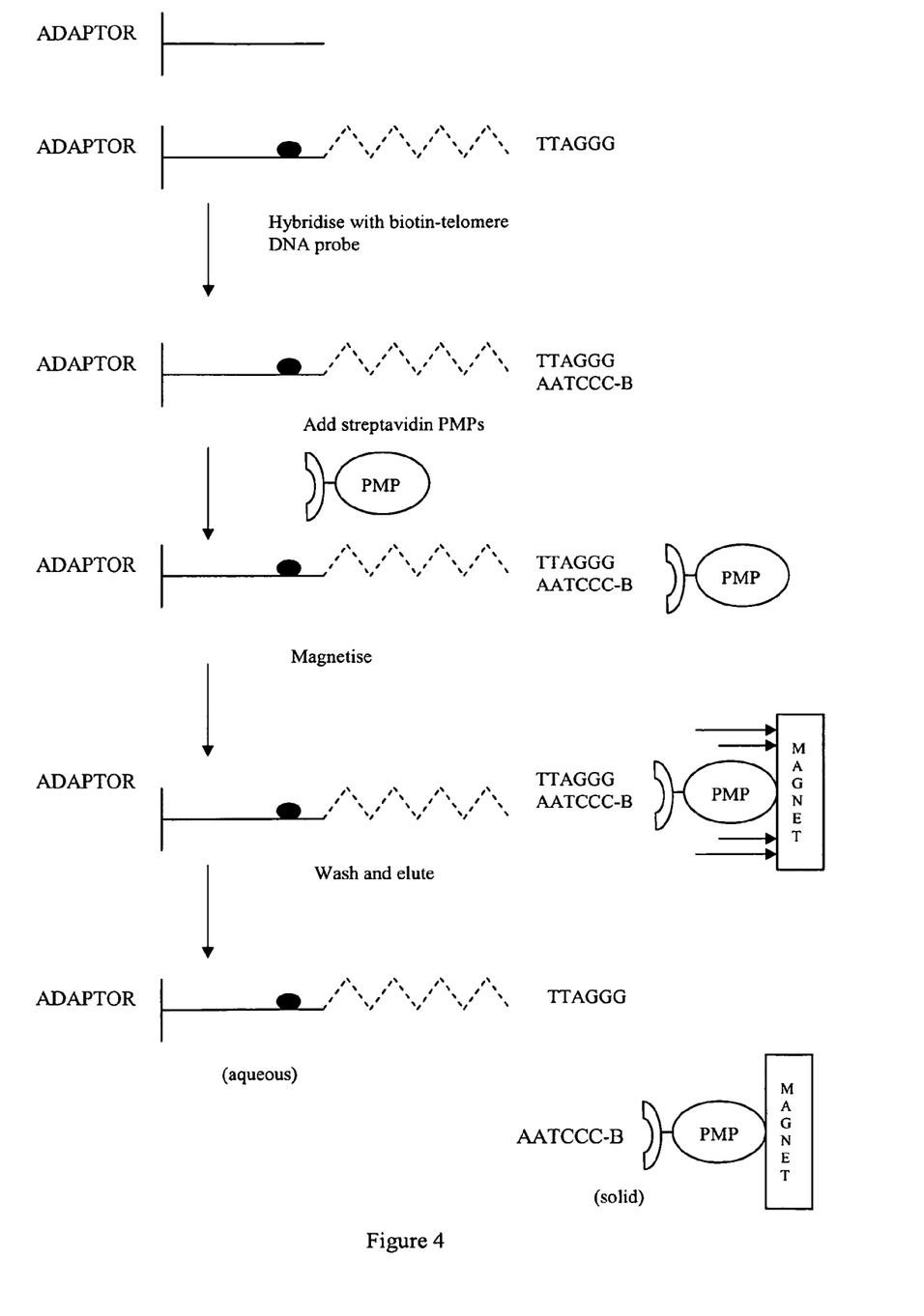
FIG. 4 illustrates diagrammatically the magnetic purification of foetal DNA using a biotinylated telomere probe.
Figure 5:
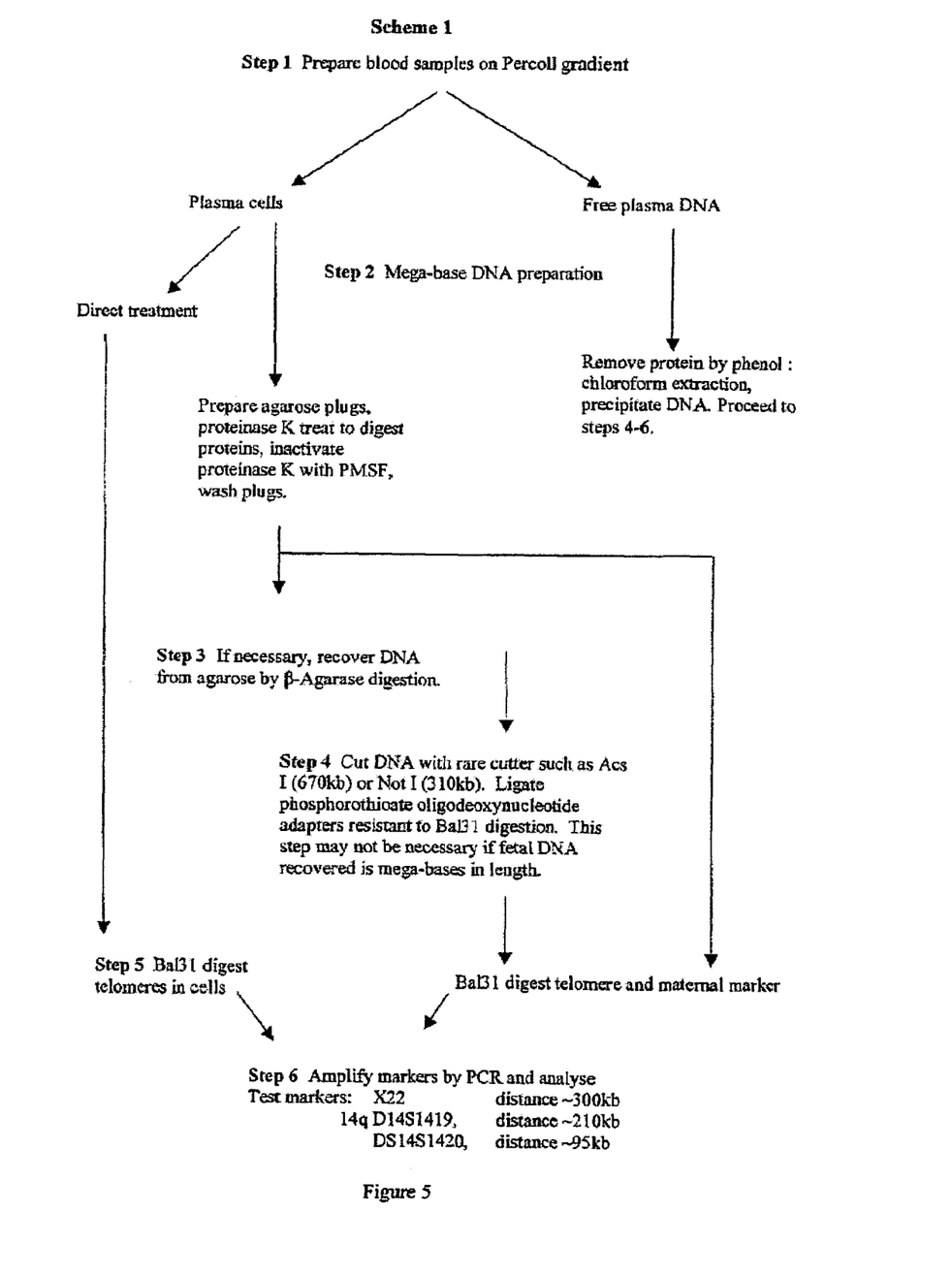
FIG. 5 illustrates a protocol for conducting analysis using the method of the invention.

Said DNA fragments may then be captured using for example streptavidin coated para-magnetic particles or beads. After separation of the magnetic particles from the supernatant, the target DNA can be released by elution of the particles (FIG. 4).

Once separated, said DNA may be amplified with a labelled primer which is specific for a particular chromosome or diagnostic region of DNA under conditions in which the primer amplifies DNA within the sample. Detection of this primer in DNA identified as being of foetal origin will therefore provide information about the foetus. Depending upon the particular diagnostic purpose, it may be useful if the second primer is specific for chromosome 18, 21 or 13, or the X or Y chromosomes. Abnormalities in chromosome number (aneuploidies) of these chromosomes are the most common.

In a particularly preferred embodiment of the invention, DNA is isolated from a maternal blood sample, for example, from cells in maternal plasma, fragmented with a restriction enzyme, and then ligated to an adaptor. The modified fragments are then incubated with an exonucleolytic enzyme such as Bal31, for a period of time which is sufficient to entirely digest maternal telomeres, but leave some foetal telomeric DNA. Further purification of teleomere-containing (foetal) DNA fragments may be achieved by magnetic separation using biotinylated telomeric probes or telomeric primers used as probes and streptavidin paramagnetic particles (PMPs) (FIG. 4).

Isolated telomere-containing (foetal) DNA fragments are then amplified by a method such as PCR, using chromosome-specific primers. Analysis is thereafter performed using a fluorescent method such as Q-PCR utilising, for instance, a DNA sequencer and Genescan software (Applied Biosystems), real time PCR or pyrosequencing.

In addition, the information obtainable using the method of the invention, in particular relating the amount of concentration of foetal DNA in the maternal sample, may be useful in prenatal screening/diagnosis as well as in diagnosis of a range of maternal conditions. These include complications in pregnancy such as pre-eclampsia, in predicting the risk of pre-term labour, and in the later development of autoimmune disease.

According to a further aspect of the invention, there is provided a kit for identifying foetal DNA in a maternal DNA-containing sample, said kit comprising means for isolating DNA from a DNA-containing sample, an exonucleolytic enzyme capable of digesting terminal regions of DNA, and a labelled primer for detecting a specific DNA sequence found in a terminal region of DNA.

The kit may contain one or more further reagents or commodities which are required for effecting the method as described above. In particular, the kit may further comprise a restriction enzyme which cuts DNA so as to produce a binding site on the DNA for an adaptor, together with the adaptor suitable for protecting the cut ends of DNA fragments from enzymatic digestion.

Depending upon the way the assay is operated, biotinylated primers and particularly biotinylated telomeric primers as well as streptavidin paramagnetic particles may also be included.

Other potential kit components include one or more additional labelled primers, such as a different fluorescently labelled primer, which is diagnostic of a chromosome condition.

The invention will now be particularly described by way of example with reference to the accompanying diagrammatic drawings in which.

BRIEF DESCRIPTION OF THE FIGURES

EXAMPLE 1

Step 1

DNA Extraction 5 mls of maternal blood was taken into each of two tubes, one of which contained EDTA. Blood samples were centrifuged at 3000 g and plasma and serum were carefully removed, into clean tubes, from the EDTA-containing and plain tubes, respectively. The plasma and serum samples were centrifuged again at 3000 g and the supernatants were transferred into clean tubes.

DNA was extracted from the plasma and serum samples using the QIAamp Blood Kit from Qiagen, according to the manufacturers' recommendations.

Step 2)

Restriction Enzyme Digest to Provide Adaptor Attachment Sites

The extracted DNA is digested with enzymes such as Notl using standard restriction enzyme digestion protocols.

Step 3)

Ligation of DNA Template and Adaptor to Protect the Proximal Ends of DNA Fragments from Digestion by Exonucleolytic Enzyme (Such as BAL 31)

This approach concerns a unidirectional DNA deletion with Bal 31 nuclease (Mukai S., Shibahara S., Morisawa H. Nucleic Acids Research Symposium Series no. 19, 1998). The principle is based on the fact that 7 bp of 2'-O-methyl ribonucleotide-DNA chimeric adapter forms greater stability and also due to steric hindrance prevents the action of nuclease attack. Therefore, ligation to Notl sites on the DNA fragments will allow digestion from one end only.

DNA and adaptor are incubated overnight at 15° C. with Ligase and buffer.

Step 4)

Digestion of Ligated DNA Templates and Adaptor with Exonucleolytic Enzyme Such as Bal 31

1 unit of Bal 31 per microgram of DNA was used to yield a uniform ladder of deletions (>1 kb) over a 20 minute period at 30° C. The reaction was stopped by adding EDTA to a final concentration of 50 mM. (FIG. 3). DNA is ethanol precipitated, to remove the high NaCl concentration from the Bal 31 reaction. Variation in conc. and/or timing of exposure is optimised for each chromosome enumeration. In the optimised situation all maternal telomeric sequences will be digested, while some of foetal telomeric DNA sequences will remain (FIG. 3a). This allows differentiation between maternal and foetal DNA fragments per se.

Extended digestion will eliminate the DNA sequences corresponding to the chromosome-specific primer site (FIG. 3b), which will allow positive identification of foetal DNA and enumeration of the respective chromosome, following Q-PCR.

Step 5)

Magnetic Purification of Foetal DNA Using Biotinylated Telomere Probe

DNA fragments are hybridised in solution with a Biotinylated telomere DNA primer by heating the DNA at 65° C. for 10 mins, adding the biotinylated primer and leaving the solution to cool down at room temperature. Thereafter streptavidin paramagnetic particles (SA-PMP) are washed with 0.5× SSC. The annealed DNA fragments and biotinylated telomeric primer are added and incubated at room temperature for 10 mins. SA-PMPs bound to the biotinylated primer are captured using a magnetic stand, and the supernatant is carefully removed. The particles are washed 4 times with 0.1× SSC. Telomere positive (foetal) fragments are eluted by resuspending the final SA-PMP particles in deionised water.

Step 6)

Q-PCR Using Chromosome Specific Polymorphic Markers

Quantitative PCR was carried out using standard methodology as described in our publication Verma et al., The Lancet 352, 9–12, 1998.

EXAMPLE 2

A protocol for conducting analysis using the method of the invention is illustrated in Scheme 1 hereinafter.

Step 1

Preparation of Blood Samples on Percoll Gradient

Blood samples are prepared on Percoll gradients and the plasma removed. Plasma cells are recovered by centrifugation using a modification of the standard protocol for discontinuous Percoll gradient (see e.g. Van Wijke et al. Clinical Chemistry 46, 5, 729–731, 2000).

In particular, 3 mls each of 40%, 45% and 50% Percoll solution (Amersham Pharmacia) in PBS, for each tube are prepared. 3 mls of EDTA blood are mixed with 3 mls of PBS in a 15 ml Polystyrol tube (Sarstedt, Roher 15 ml tubes cat no. 62.553.042). 3 ml of 40% Percoll is introduced as an underlayer using a canula (B. Braun, Filter Straw cat no. 415020) attached to a 5 ml syringe. The tip of the canula is placed at the bottom of the tube going through the blood and the Percoll solution ejected slowly. Using the same canula, the underlayering process is then repeated twice with 45% and 50% Percoll respectively. In each case, the tip of the canula is placed at the bottom of the tube and the ejection is made carefully so as not to disturb the gradients.

In general 3–4 tubes will be prepared in this way for each sample under test. The prepared tubes are then centrifuged (without using the centrifuge brakes) at 500 g for 30 minutes at 18–20° C.

After this, the tubes are removed and the plasma (top) layer taken off and put in a clean tube. Plasma from different tubes from the same sample may be added together to ensure that there is about 6 mls of fluid in each tube. This is then centrifuged again at 500 g for 20 minutes, this time with the brakes on. The resultant cell pellet is then washed in 6 ml of PBS a couple of times.

Step 2

Extraction of High Molecular Weight DNA

Plasma cells[1] are resuspended in PBVS at $2\times10^5$ cells per 50 μl[2]. Equal amounts of agarose solution (1.9% NuSieve GTG) are added to cell suspension-containing $1\times10^5$ cells. 50 μl are dispensed into molds and allowed to set. Agarose plugs are then treated in: 0.5M EDTA, pH 8.0, 1% N-Laurylsarcrosine, 2 mg/ml Proteinase K for 24–72 hours at 50° C. (although O/N incubation may be sufficient for our downstream applications). This treatment digests cell membrane allowing penetration of enzymes in later stages. The agarose plugs are then washed in water and incubated at 50° C. in PMSF (a protease inhibitor) to fully inactivate any remaining Proteinase K that will effect enzymatic treatment. Agarose plugs are then washed and stored at 4° C.

Note:

[1.] 3 ml blood contains~$2\times10^3$ plasma cells

[2.] $1\times10^5$ cells=1 μl DNA

Plasma DNA is extracted with phenol:chloroform (1:1), ethanol precipitated, washed twice in 70% ethanol and carefully resuspended in water.

Step 3

Ligation of Nuclease Resistant Adapters

This procedure may be omitted if the ligation of adapters is unnecessary, as this is the only step that is affected by the DNA being in the agarose plugs. Both Bal31 digestion and the PCR reaction will be unaffected by the agarose plugs. The protocol allows the agarose to be digested into alcohol soluble oligosaccharides, this makes the DNA more accessible without damaging or shearing the DNA. The agarose plugs are melted and an equal volume of 50× buffer is added plus 1 U β-Agarase incubated at 45° C. for 60 minutes. The remaining oligosaccharides and β-Agarase do not interfere with subsequent enzymatic reactions.

For the ligation of adapters the DNA will have to be cut with a rare cutter such as Asc I or Not I which cut within the human genome~every 670 kb and 310 kb respectively. This will produce compatible ends for the adapter to ligate to, restriction sites between the telomere and marker will have to be checked to ensure that these enzymes do not cut within this region. Equilibrate the agarose plug in 100 μl of 1× restriction buffer with 10 U of enzyme, incubate for 2 hours and then rinse with water.

Complementary oligonucleotides containing phosphorothioate links will be annealed to produce adapters resistant to nuclease digestion. They will also contain cohesive ends complementary to the restriction endonuclease used to cleave the DNA samples. These adapters will be ligated by the addition of 1× ligation buffer, 5 U Ligase and incubated at 37° C. for 2 hours.

Step 4

Bal31 Nuclease Digestion of Telomere Ends

Agarose plugs containing high molecular weight DNA are equilibrated for 30 minutes in 1 ml of 1× Bal31 buffer with 50 U of enzyme (NEBL) on ice for 30 minutes. Digestion is effected by placing the reaction at 30° C., removing plugs at each time point i.e. 0, 30, 60, 90 and 120 minutes and placing in 1 ml ice-cold TE. Bal31 is removed by rinsing plugs in water for 30 minutes on ice. Bal31 should be completely inactivated during the heat denaturation step of the PCR. Time points are taken initially to establish the length of digestion needed to remove the required length of DNA to allow discrimination of the fetal DNA with the longer telomeres.

Step 5

Amplification of Polymorphic Markers by QF-PCR

Polymorphic markers are amplified by QF-PCR using standard technology (see e.g. Verma et al., Lancet, 352, 9–12, 1998; Pertl et al., Amer. J. Obstet. Gynecol. 177, 4, 899–906).

The X22 marker (~300 kb from telomere) is a particular marker which may be amplified in this way, but other telomeric polymorphic markers may be selected depending upon the particular aims of the diagnosis. For example, two highly polymorphic markers on chr14 D14S1419 and D14S1420 are located at ~210 kb and 95 kb from the telomere.

EXAMPLE 3

Non-Invasive Prenatal Diagnosis of Foetal Trisomy 21 Down Syndrome Using the Methods of the Invention

EXAMPLE 3A

1. Pregnancy and Blood Sample 12 ml of blood was drawn into 2 edetic acid (EDTA) tubes by venipuncture from a pregnant woman at 12 weeks gestational age, following written informed consent with Ethical Approval from the Local Ethical Committee.

2. Isolation of Cells from the Nuclear Compartment and Plasma

Both nucleated cells from the nuclear compartment and from plasma were isolated from the maternal blood using a Triple Density Gradient according to the protocol as described (Ganshirt et al., Diagnostic Cytogenetics, Springer Lab Manual, 1999 R. -D. Wagner, Fetal Cells in Maternal blood, pp 401–415) with slight modifications.

12 ml of the EDTA blood is added to 12 ml of Phosphate Buffer Solution (PBS) and mixed by inverting the tube. 6 ml of the blood/PBS mixture is pippetted into four 15 ml polystyrol tubes. Three layers of Percoll® (Amersham Pharmacia) are underlayered, using a long and thin canula attached to a syringe. Initially 3 ml of 40% Percoll is underlayered, followed by 3 ml of 45% and 3 ml of 50% Percoll. The suspension is then centrifuged at 500 g for 30 min. The plasma layer and the lymphocyte layer are removed and transferred to clean tubes and again centrifuged at 500 g for 10 min. The cell pellet is washed in PBS and transferred to microtubes containing 5 µl proteinase K solution (400 mg/l proteinase K, 20 mmol/l dithiothreitol, 1.7 µmol/l sodium dodecyl sulfate, 10 mmol/l Trisbuffer, 50 mmol/l potassium chloride).

3. Extraction of High Molecular Weight DNA

Plasma cells are resuspended in PBVS at $2\times10$ cells per 50 µl. Equal amounts of agarose solution (1.9% NuSieve GTG) are added to the cell suspension, containing $1\times10^5$ cells. 50 µl are dispensed into molds and allowed to set. Agarose plugs are then treated in: 0.5M EDTA, pH 8.0, 1% N-Laurylsarcrosine, 2 mg/ml Proteinase K for 24–72 hours at 50° C. The agarose plugs are then washed in water and incubated at 50° C. in PMSF (a protease inhibitor) to fully inactivate any remaining Proteinase K that will effect enzymatic treatment.

4. Ligation of Nuclease Resistant Adapters

The agarose plugs are melted and an equal volume of 50× buffer is added plus 1 U β-Agarase and incubated at 45° C. for 60 minutes. The agarose plug is equilibrated in 100 µl of 1× restriction buffer with 10 U of enzyme, incubated for 2 hours and then rinsed with water.

These adapters are then ligated by the addition of 1× ligation buffer, 5 U Ligase and incubated at 37° C. for 2 hours.

5. Bal31 Nuclease Digestion of Telomere Ends

Agarose plugs containing high molecular weight DNA are equilibrated for 30 minutes in 1 ml of 1× Bal31 buffer with 5 U of enzyme (NEBL) on ice for 30 minutes. Digestion is effected by placing the reaction at 30° C., removing plugs at each time point i.e. 0, 30, 60, 90 and 120 minutes and placing in 1 ml ice-cold TE. Bal31 is removed by rinsing plugs in water for 30 minutes on ice.

6. Amplification of Polymorphic Markers by QF-PCR

A multiplex fluorescence PCR assay is applied by routine technology (see e.g. Pertl et al 1997 Am. J. Obstet. Gynecol. 177, 899–906) using primers for D21S1411 and D21S1446. Each of the forward primers is labelled (5' end) with a fluorescent dye to enable visualisation and analysis of the PCR product. After the initial denaturation, 24 cycles of 95° C. for 48 sec, 60° C. for 48 sec, and 72° C. for 1 min is performed, followed by an extension of 72° C. for 15 min.

7. Analysis

The allelic fragments are resolved on a 6% denaturing polyacrylamide gel, and analysed on an Applied Biosystems (Warrington) 373 DNA sequencer running Genescan 672 software. Amplification products are sized, and their fluorescence intensities calculated, based on the areas of the peaks seen on the electropherograms. Analysis was performed on (a) DNA from lymphocytes of the maternal blood sample directly, (b) DNA from same type of cells after enzymatic digestion, and (c) DNA from cells in the plasma component of the maternal sample (expected to contain an enrichment of fetal cells) after enzymatic digestion.

8. Results (a) The electropherogram obtained from PCR products of DNA of the lymphocytes of the maternal blood sample shows the occurrence of two equal sized peaks for each of the two primers D21S1411 and D21S1446. This result is the expected from a normal female.

(b) The electropherogram obtained from PCR products of DNA of the lymphocytes from the maternal blood sample, following enzymatic exonucleolytic digestion with 2 Units of Bal31 for 20 min, shows absence of signals for the most distal marker D21S1446, while two equal sized signals are seen at positions for the proximal marker D21S1411.

This indicates that these conditions for enzymatic digestion are optimal for our purposes of differentiating between maternal and fetal DNA.

(c) The electropherogram obtained from the DNA of cells in maternal plasma, following enzymatic digestion under same conditions as in (b) shows unclear signals for the proximal marker D21S1411 but three clear signals for the distal marker D21S1446.

This result indicates first of all that the telomeric DNA sequences have been entirely eliminated (both from maternal and fetal DNA). Secondly, the unclear signal of the DNA sequences of the proximal marker D21S1411, is interpreted to be caused by a mixture of maternal and fetal DNA. Thirdly, we conclude that the three clear signals of the distal marker D21S1446 (one of which is located in a position, which is not the same as the maternal as seen in the electropherogram of the DNA from the lymphocytes of the maternal blood sample), are fetal, and shows that the fetus has trisomy 21.

SUMMARY

This example illustrates that it is possible to routinely enumerate numbers of chromosomes 21 and thus identify foetal trisomy 21 Down syndrome by DNA analysis of a maternal blood sample, following enzymatic digestion of telomeric and subtelomeric DNA sequences. The process is rapid with results available within the same day of arrival of the blood sample in the laboratory. Furthermore, substantial automation is possible.

EXAMPLE 3B

1. Pregnancy and Blood Sample 12 ml of blood was drawn into 2 edetic acid (EDTA) tubes by venipuncture from a pregnant woman at 12 weeks gestational age, following written informed consent with Ethical Approval from the Local Ethical Committee.

2. Isolation of Cells from the Nuclear Compartment and Plasma

Both nucleated cells from the nuclear compartment and from plasma were isolated from the maternal blood using a Triple Density Gradient according to the protocol as described (Ganshirt et al., Diagnostic Cytogenetics, Springer Lab Manual, 1999 R. -D. Wagner, Fetal Cells in Maternal blood, pp 401–415) with slight modifications.

12 ml of the EDTA blood is added to 12 ml of Phosphate Buffer Solution (PBS) and mixed by inverting the tube. 6 ml of the blood/PBS mixture is pippetted into four 15 ml polystyrol tubes. Three layers of Percoll® (Amersham Pharmacia) are underlayered, using a long and thin canula attached to a syringe. Initially 3 ml of 40% Percoll is underlayered, followed by 3 ml of 45% and 3 ml of 50% Percoll. The suspension is then centrifuged at 500 g for 30 min. The plasma layer and the lymphocyte layer are removed and transferred to clean tubes and again centrifuged at 500 g for 10 min. The cell pellet is washed in PBS and transferred to microtubes containing 511 proteinase K solution (400 mg/l proteinase K, 20 mmol/l dithiothreitol, 1.7 µmol/l sodium dodecyl sulfate, 10 mmol/lTrisbuffer, 50 mmol/l potassium chloride).

3. Exonucleolytic Enzyme Digestion 1 unit of Bal31 per microgram of DNA was used to yield a uniform ladder of deletions (>1 kb) over a 20 minute period at 30° C. The reaction was stopped by adding EDTA to a final concentration of 50 mM.

Enzymatic digestion is first performed on DNA of lymphocytes to calibrate the concentration and time required for optimal elimination of DNA sequences to allow differentiation between fetal and maternal DNA. The primers chosen in this case are D21S1446 and D21S1411 at 21q22.3 (with D21S1411 being located proximal to D21S1446) together with the primer for the telomere DNA sequence TTAGGG.

The optimal conditions to discriminate between maternal and fetal signals was set for elimination of telomeres plus the marker D21S1446 in DNA of lymphocytes of the maternal blood sample (primarily maternal cells). This was evaluated as described in steps 4 and 5. The enzymatic digestion of cells isolated from maternal plasma (a mixture of maternal cells with an enrichment of fetal cells) was then exposed to Bal31 under these verified optimal conditions.

4. Multiplex PCR

A multiplex fluorescence PCR assay is applied by routine technology (see e.g. Pertl et al., 1997 Am. J. Obstet. Gynecol. 177, 899–906) using primers for D21S1411 and D21S1446. Each of the forward primers was labelled (5' end) with a fluorescent dye to enable visualisation and analysis of the PCR product. After the initial denaturation, 24 cycles of 95° C. for 48 sec, 60° C. for 48 sec, and 72° C. for 1 min was performed followed by an extension of 72° C. for 15 min.

5. Analysis

The allelic fragments were resolved on a 6% denaturing polyacrylamide gel, and analysed on an Applied Biosystems (Warrington) 373 DNA sequencer running Genescan 672 software. Amplification products were sized, and their fluorescence intensities were calculated, based on the areas of the peaks seen on the electropherograms. Analysis was performed on (a) DNA from lymphocytes of the maternal blood sample directly, (b) DNA from same type of cells after enzymatic digestion, and (c) DNA from cells in the plasma component of the maternal sample (expected to contain an enrichment of fetal cells) after enzymatic digestion.

6. Results (a) The electropherogram obtained from PCR products of DNA of the lymphocytes of the maternal blood sample shows the occurrence of two equal sized peaks for each of the two primers D21S1411 and D21S1446. This result is the expected from a normal female.

(b) The electropherogram obtained from PCR products of DNA of the lymphocytes from the maternal blood sample, following enzymatic exonucleolytic digestion with 2 units of Bal31 for 20 min shows absence of signals for the most distal marker D21S1446, while two signals are seen at positions for the proximal marker D21S1411.

This indicates that these conditions for enzymatic digestion are optimal for our purposes of differentiating between maternal and fetal DNA.

(c) The electropherogram obtained from the DNA of cells in maternal plasma, following enzymatic digestion under same conditions as in (b) shows unclear signals for the proximal marker D21S1411 but three clear signals for the distal marker D21S1446.

This result indicates first of all that the telomeric DNA sequences have been entirely eliminated (both from maternal and fetal DNA). Secondly, the unclear signal of the DNA sequences of the proximal marker D21S1411, is interpreted to be caused by a mixture of maternal and fetal DNA. Thirdly, we conclude that the three clear signals of the distal marker D21S1446 (one of which is located in a position, which is not the same as the maternal as seen in the electropherogram of the DNA from the lymphocytes of the maternal blood sample), are fetal, and shows that the fetus has Trisomy 21.

SUMMARY

This example illustrates that it is possible to routinely enumerate numbers of chromosomes 21 and thus identify foetal trisomy 21 Down syndrome by DNA analysis of a maternal blood sample, following enzymatic digestion of telomeric and subtelomeric DNA sequences. In this examples DNA is less degraded, and it has therefore been possible to perform the diagnostic analysis without the application of an adaptor. As with Example 3A analysis is rapid with results available within the same day of arrival of the blood sample in the laboratory; and substantial automation is possible.

The invention claimed is:

1. A method for the identification of foetal DNA in sample containing both maternal and foetal DNA, said method comprising (a) isolating DNA from said sample, (b) subjecting said DNA to exonucleolytic digestion by an enzyme so as to remove end regions of said DNA, and (c) detecting the presence of a DNA sequence remaining in foetal DNA but absent from maternal DNA as a result of said digestion process.

2. A method according to claim 1 wherein said maternal DNA-containing sample is a blood or vaginal sample.

3. A method according to claim 1 wherein in a preliminary step, cells are first isolated from maternal plasma, and DNA then isolated from these in step (a).

4. A method according to claim 1 wherein DNA from step (a) is cut using a restriction enzyme into fragments prior to step (b).

5. A method according to claim 4 wherein cut ends of the DNA fragments are protected prior to the exonucleolytic digestion so that they are not susceptible to digestion by the exonucleolytic enzyme.

6. A method according to claim 5 wherein the restriction enzyme used to form the DNA fragments cuts and provides binding sites for a protecting moiety, and protection is achieved by ligation of that protecting moiety.

7. A method according to claim 6 wherein the protecting moiety is an adaptor.

8. A method according to claim 7 wherein the adaptor is 2'-O-methyl ribonucleotide DNA or a complementary oligonucleotide containing phosphorothioate links.

9. A method according to claim 1 wherein foetal DNA is isolated from maternal DNA.

10. A method according to claim 9 wherein foetal DNA fragments are separated by hybridising biotinylated probes specific for teleomere DNA sequences remaining in foetal DNA after digestion, to said DNA and thereafter immobilising said probes to a streptavidin covered support.

11. A method according to claim 10 wherein said strepavidin covered support comprises a paramagnetic particle.

12. A method according to claim 1 wherein the said DNA sequence remaining in foetal DNA is a telomere sequence or a chromosome marker located proximal the telomere region.

13. A method according to claim 12 wherein said DNA sequence remaining in foetal DNA is a telomere sequence.

14. A method according to claim 12 wherein said DNA sequence remaining in foetal DNA is a sub-telomeric polymorphic chromosome-specific marker.

15. A method according to claim 1 wherein the said DNA sequence is detected using a first labelled probe which is specific for said sequence.

16. A method according to claim 15 wherein said label is a fluorescent label.

17. A method according to claim 1 wherein the exonucleolytic enzyme is Bal31.

18. A method according to claim 1 wherein exonucleolytic digestion is effected in stages in which, in a first step, 3' extension DNA is removed, in a second step, 3'–5' ss regions are excised and in a third step, ss regions are digested.

19. A method according to claim 18 wherein the first step is effected using Mungbean nuclease.

20. A method according to claim 18 wherein the second step is effected using Exonuclease III.

21. A method according to claim 18 wherein the third step is effected using Mungbean nuclease.

22. A method according to claim 1 wherein the amount of DNA of foetal origin in the sample is determined.

23. A method according to claim 1 wherein foetal DNA in the sample is amplified.

24. A method according to claim 23 wherein the amplification is effected using the polymerase chain reaction (PCR).

25. A method according to claim 24 wherein PCR is used to quantitate the amount of foetal DNA in the sample, or the amplified sample is subjected to genetic analysis.

26. A method according to claim 1 wherein foetal DNA identified is subjected to pre-natal diagnosis.

27. A method according to claim 26 wherein the diagnosis detects chromosome aberrations.

28. A method according to claim 1 wherein before step (c), DNA is separated according to size.

29. A method according to claim 25 wherein separated DNA identified as being of foetal origin is amplified with a labelled primer which is specific for a particular chromosome or diagnostic region of DNA.

30. A method according to claim 29 wherein said labelled primer carries a fluorescent label.

31. A method according to claim 25 wherein foetal DNA is amplified using a fluorescently labelled primer, and the amplified sequence is diagnostic for a chromosome or DNA condition.

32. A method according to claim 31 wherein said primer amplifies a sequence which is specific for chromosome 18, 21, 13, X or Y.

33. A method according to claim 25 which is used in the diagnosis of conditions of the mother.

34. A method according to claim 33 wherein the conditions are pre-eclampsia, in predicting the risk of pre-term labour, and in the later development of autoimmune disease.

35. A kit for identifying foetal DNA in a maternal blood or vaginal sample, said kit comprising means for extracting DNA from a blood or vaginal sample, an exonucleolytic enzyme capable of digesting DNA, and a labelled primer suitable for detecting a specific DNA sequence found in a terminal region of DNA.

36. A kit according to claim 35 which further comprises a restriction enzyme which cuts DNA so as to produce a binding site on the DNA for an adaptor suitable for protecting the cut ends of DNA fragments from enzymatic digestion.

37. A kit according to claim 35 which further comprises an adaptor suitable for protecting the ends of DNA fragments from enzymatic digestion.

38. A kit according to claim 35 which further comprises a biotinylated telomeric probe.

39. A kit according to claim 38 which further comprises streptavidin coated paramagnetic particles.

40. A kit according to claim 35 which comprises a labelled primer which is diagnostic of a chromosome condition.

* * * * *